US008183284B2

(12) United States Patent
Sprafka, II et al.

(10) Patent No.: US 8,183,284 B2
(45) Date of Patent: May 22, 2012

(54) COMPOSITIONS FOR REDUCING THE INCIDENCE OF DRUG INDUCED ARRHYTHMIA

(75) Inventors: Joseph Michael Sprafka, II, Loveland, OH (US); Jose Mauro Goulart-Brum, Loveland, OH (US)

(73) Assignee: Warner Chilcott Company, LLC, Fajardo, PR (US)

( * ) Notice: Subject to any disclaimer, the term of this patent is extended or adjusted under 35 U.S.C. 154(b) by 0 days.

(21) Appl. No.: 11/489,756

(22) Filed: Jul. 20, 2006

(65) Prior Publication Data

US 2007/0021395 A1 Jan. 25, 2007

Related U.S. Application Data

(60) Provisional application No. 60/701,555, filed on Jul. 22, 2005.

(51) Int. Cl.
*A01N 43/08* (2006.01)
*A61K 31/34* (2006.01)

(52) U.S. Cl. .......................... 514/468; 514/461; 514/471

(58) Field of Classification Search .................. 514/468, 514/461, 471
See application file for complete search history.

(56) References Cited

U.S. PATENT DOCUMENTS

| | | | |
|---|---|---|---|
| 3,882,228 A | 5/1975 | Boncey et al. | |
| 3,887,700 A | 6/1975 | Boncey et al. | |
| 5,328,909 A | 7/1994 | Ando et al. | |
| 5,416,117 A | 5/1995 | Ando et al. | |
| 5,422,359 A | 6/1995 | Ando et al. | |
| 5,981,555 A | 11/1999 | Kuhrts et al. | |
| 6,103,742 A | 8/2000 | Ikeda et al. | |
| 6,245,797 B1 | 6/2001 | Winokur | |
| 6,316,487 B1 * | 11/2001 | Druzgala et al. | 514/419 |
| 2003/0119794 A1 | 6/2003 | Bacaner et al. | |
| 2004/0137054 A1 | 7/2004 | Hager et al. | |
| 2004/0248820 A1 | 12/2004 | D'Amato | |
| 2005/0070552 A1 * | 3/2005 | Fedida et al. | 514/255.06 |
| 2005/0101565 A1 | 5/2005 | Dasseux | |
| 2005/0142129 A1 | 6/2005 | Mangano | |
| 2005/0142180 A1 | 6/2005 | Bisgaier et al. | |
| 2005/0143354 A1 | 6/2005 | Verbeuren et al. | |

FOREIGN PATENT DOCUMENTS

| | | |
|---|---|---|
| GB | 742544 | 12/1955 |
| GB | 1025862 | 4/1966 |
| GB | 1142757 | 2/1969 |
| GB | 1269181 | 4/1972 |
| GB | 1287475 | 8/1972 |
| GB | 2253348 A | 9/1992 |
| JP | 58-126879 A | 7/1983 |
| JP | 2002-534379 A | 10/2002 |
| WO | 87/05297 A1 | 9/1987 |
| WO | 90/09185 A1 | 8/1990 |
| WO | 00/40232 A2 | 7/2000 |
| WO | WO 03/086415 A1 | 10/2003 |
| WO | 2005/018635 A2 | 3/2005 |

OTHER PUBLICATIONS

Page et al, Circulation 107(8):1141-1145, 2003.*
Khan et al, Novel therapeutics for treatment of long-QT syndrome and torsade de pointes, International Journal of Cardiology vol. 95, Issue 1, May 2004, pp. 1-6.*
Sra et al, Curr Probl Cardiol (2000) vol. 25, Issue 7, 413-524.*
Siu et al (The American Journal of Cardiology, vol. 92, Iss. 11 (Dec. 2003) pp. 1343-1345).*
Kamath et al, European Heart Journal 22(24) (2001) pp. 2233-2242.*
Aronow, W.S., "Therapy of Older Persons With Ventricular Arrhythmias", Annals of Long-Term Care, vol. 8, issue 8, Aug. 2000.
Baker, K.E. et al., "Left regional cardiac perfusion in vitro with platelet-activating factor, norepinephrine and K+ reveals that ischaemic arrhythmias are caused by independent effects of endogenous 'mediators' facilitated by interactions, and moderated by paradoxical antagonism", British Journal of Pharmacology, 2004, 142, pp. 352-366.
Brode, S.E. et al., "ICD-antiarrythmic drug and ICD-pacemaker interactions," J. Cardiovasc Electrophysiol. Jul. 1997; 8(7):830-42.
Chen, J. et al., "Pravastatin Prevents Arrhythmias Induced by Coronary Artery Ischemia/Reperfusion in Anesthetized Normocholesterolemic Rats", J. Pharmacol Sci., 93, pp. 87-94, 2003.
Faber, T. S. et al., "Drug-induced torsade-de-pointes: Incidence, management and prevention", Drug Safety, vol. 11, No. 6, 1994, pp. 463-476.
Gillis, A.M., "Effects of antiarrhythmic drugs on QT interval dispersion—Relationship to antiarrhythmic action and proarrhythmia", Progress in Cardiovascular Diseases, 2000, vol. 42, No. 5, pp. 385-396.
Gold, M.R. et al., "Cardiac Arrhythmia: Current therapy", Hosp Pract (Minneap). Sep. 1, 1999; 34(9):27-8, 31-2, 35-8.
Gowda, R. M. et al., "Torsade de pointes: the clinical considerations", International Journal of Cardiology, vol. 96, No. 1, Jul. 2004, pp. 1-6.
Mark, L. et al., "The effect of fluvastatin on QT dispersion and lipid levels", Kardiologia Polska, 2001, vol. 55, No. 11, pp. 386-388.
Mitchell, L.B. et al., "Increased QT interval dispersion in patients with amiodarone-associated torsade de pointes ventricular tachycardia", Canadian Journal of Cardiology, vol. 16, No. Supplement F, Sep. 2000, p. 227F.
Nazeer, S. MD, "Torsade de Pointes", http://emedicine.com, Jul. 6, 2005.

(Continued)

*Primary Examiner* — Benjamin Packard
(74) *Attorney, Agent, or Firm* — Fitzpatrick, Cella, Harper & Scinto

(57) ABSTRACT

In accordance with the present invention, novel methods and formulations are provided for treating and preventing the incidence of drug-induced pro-arrhythmia, including torsades de pointes. The methods and formulations comprise a combination of a drug that induces torsade de pointes, such as Class III antiarrhythmics, certain antimicrobials, antihistamines, antidepressants, antipsychotics, diuretics, with an aspirin and/or a statin. In certain embodiments, the compositions and methods for treatment comprise azimilide and aspirin and/or a statin. These compositions may be administered by different routes, including orally. In certain embodiments where the antiarrhythmic is azimilide it may be administered orally in a dose of about 25 mg to about 300 mg.

23 Claims, No Drawings

OTHER PUBLICATIONS

Page, R.L. et al., "Asymptomatic or "Silent" Atrial Fibrillation Frequency in Untreated Patients and Patients Receiving Azimilide," Circulation, Mar. 4, 2003, pp. 1141-11145.

Roden, D.M., "Current status of class III antiarrhythmic drug therapy", Am J. Cariol. Aug. 26, 1993;72(6);44B-49B Abstract.

Ruscin, J.M. et al., "Newer Pharmacologic Agents and Their Relevance to Older Adults", Annals of Long-Term Care, vol. 9, issue 10, Oct. 2001.

Tong, K.L. et al., "A Case Series of Drug-Induced Long QT Syndrome and Torsade de Pointes", Singapore Med. J., 2001 vol. 42(12):566-570.

Tse, H.F. et al., "Current Therapeutics: Management of Atrial Fibrillation", Hong Kong Practitioner 19(11) Nov. 1997.

Zalewski, J., "Dofetilide: A New Class III Antiarrhythmic," Center for Continuing Education, The Cleveland Clinic, vol. III, No. IV, Sep./Oct. 2002.

Joynt et al., "Effect of Angiotensin-Converting Enzyme Inhibitors, Beta Blockers, Statins, and Aspirin on C-Reactive Protein Levels in Outpatients With Heart Failure," The American Journal of Cardiology 93:783-85 (2004).

Office Action in Colombian Patent Application No. 08.005.058, issued Jun. 3, 2011, 18 pages.

First Examination Report in Indian Patent Application No. 425/DELNP/2008, issued Apr. 7, 2011, 2 pages.

Camm et al., "Mortality in Patients After a Recent Myocardial Infarction. A Randomized, Placebo-Controlled Trial of Azimilide Using Heart Rate Variability for Risk Stratification," Circulation 109:990-96 (2004).

Lorenz et al., "Do statins influence the prognostic impact of non-sustained ventricular tachycardia after ST-elevation myocardial infarction?" European Heart Journal 26:1078-85 (2005).

Belardinelli et al., "Assessing predictors of drug-induced torsade de pointes", Trends in Pharmacological Sciences, vol. 24, No. 12, pp. 619-625 (Dec. 2003).

Hohnloser et al., "Amiodarone-associated Proarrhythmic Effects, A Review with Special Reference to Torsade de Pointes Tachycardia", Annals of Internal Medicine, vol. 121, No. 7, pp. 529-535 (Oct. 1, 1994).

Wilkerson et al., "Influence of Nonsteroidal Anti-Inflammatory Drugs on Ouabain Toxicity," American Heart Journal, vol. 94, No. 4, pp. 454-459 (1977).

S. Singh, "Internal Cardioverter Defibrillator (ICD) and Antiarrhythmic Drug Interaction", http://www.americanheart.org/presenter, 2 pages, printed Jul. 12, 2005.

The Arrhythmia Service, "Current Treatments", http://www.arrhythmia.org/current_treatment.html, 4 pages, printed Jul. 14, 2005.

Touboul, "Securite des nouveaux agents anti-arythmiques", Archives Des Maladies du Coeur et Des Vaisseaux, Tome 97, No. 4, pp. 313-316 (Apr. 2005).

Pratt et al., "Cumulative Experience of Azimilide-Associated Torsades de Pointes Ventricular Tachycardia in the 19 Clinical Studies Comprising the Azimilide Database," J. Am. Coll. Cardiol, vol. 48, No. 3, pp. 471-477 (2006).

* cited by examiner

COMPOSITIONS FOR REDUCING THE INCIDENCE OF DRUG INDUCED ARRHYTHMIA

CROSS REFERENCE TO RELATED APPLICATION

This invention claims the benefit under 35 USC 119(e) to U.S. Application No. 60/701,555, filed Jul. 22, 2005.

FIELD OF THE INVENTION

This invention provides methods and formulations for treating and preventing the incidence of drug induced pro-arrhythmia. In certain embodiments the drugs are for the treatment of cardiac arrhythmia and the methods and formulations of the present invention further reduce the incidence of torsades de pointes. In certain embodiments the methods and formulations may comprise a combination of a Class III anti-arrhythmic with an aspirin and/or statin.

BACKGROUND OF THE INVENTION

Ventricular tachycardias (VT) are triggered by electrical or mechanical intervention in the propagation of electric impulses generated at pace-making regions of the heart. This interference can be initiated by electrolyte disturbance, myocardial damage by disease, genetic defects, medications or conditions such as prolonged ischemia. The most common cause of VT is myocardial ischemia and infarction.

The control of life-threatening arrhythmias and the prevention of sudden cardiac arrhythmia has been a difficult challenge for modem cardiology. Large-scale, randomized, controlled trials have greatly contributed to our understanding of the management of life-threatening arrhythmias. Available treatments for the management of ventricular arrhythmia include antiarrhythmic drugs, implantable cardioverter defibrillators (ICDs) and catheter ablation. Each therapy provides unique advantages for selected patients with life-threatening arrhythmias.

Any drug that prolongs the action potential duration of cardiac cells (as measured by increases in QT interval from the electrocardiogram) may be proarrhythmic. Antiarrhythmics that prolong the action potential duration of cardiac cells are among the most effective class of agents to treat arrhythmias however their use carries a considerable risk of torsades de pointes (TdP). Torsades de pointes is a form of polymorphic ventricular tachycardia that can cause death and results when there is prolonged QT intervals. Besides Class III antiarrhythmics, other drugs that are known to have a risk of causing TdP include but are not limited to some Class I, antimicrobials, antihistamines, antipsychotics, etc, Ramesh M. Gowda et al., "Review Torsade de pointes: the clinical considerations," *International Journal of Cardiology*, 96 (2004) 1-6. Thus, anything that reduces the incidence of TdP will reduce pro-arrhythmia in general and improve the safety of otherwise effective drugs.

Aspirin is often used as an analgesic (against minor pains and aches), antipyretic (against fever), and anti-inflammatory. It also has an anticoagulant (blood thinning) effect and is used in long-term low-doses to prevent heart attacks. Statins are used to slow the progression of atherosclerosis that causes chest pain, heart attacks, strokes, and intermittent claudication in individuals who have or are at risk for atherosclerosis. The statins play an important role in the primary and secondary prevention of coronary heart disease and myocardial infarction. Research continues into other areas where statins appear to have an effect: inflammation, dementia, and neoplasm (tumors).

SUMMARY OF THE INVENTION

In accordance with the present invention, novel methods and formulations are provided for treating and preventing the incidence of drug-induced pro-arrhythmia, including torsades de pointes. The methods and formulations comprise a combination of a drug that induces torsade de pointes, such as Class III antiarrhythmics, certain antimicrobials, antihistamines, antidepressants, antipsychotics, diuretics, with an aspirin and/or a statin. In certain embodiments, the compositions and methods for treatment comprise azimilide and aspirin and/or a statin. These compositions may be administered by different routes, including orally. In certain embodiments where the antiarrhythmic is azimilide it may be administered orally in a dose of about 25 mg to about 300 mg.

DETAILED DESCRIPTION OF THE INVENTION

Aspirin or acetylsalicylic acid is a drug in the family of salicylates.

The term "statin" refers to a class of lipid-lowering drugs that reduce serum cholesterol levels by inhibition of HMG-CoA reductase. Non-limiting examples of statins useful herein include the following: atorvastatin, fluvastatin, lovastatin, pravastatin, rosuvastatin, simvastatin and cerivastatin.

The terms "antiarrhythmic agent" and "antiarrhythmic drug," as used herein, include any pharmaceutically active form of a Class I or Class III antiarrhythmic including, but not limited to, acids, salts, esters, polymorphs, solvates, and derivatives thereof. Non-limiting examples of antiarrhythmic drugs useful herein include the following: azimilide, sotalol (including combinations of d,1-sotalol, i.e., racemic sotalol), amiodarone, dofetilide, cibenzoline, and bunafitidine. Although any form (e.g., salt, base or amide form) may be used, a salt form is preferred with azimilide, sotalol and amiodarone. In one embodiment the active agent herein is azimilide dihydrochloride.

A "pharmaceutically-acceptable salt" is a cationic salt formed at any acidic (e.g., hydroxamic or carboxylic acid) group, or an anionic salt formed at any basic (e.g., amino) group. Many such salts are known in the art, as described in WO 87/05297, by Johnston et al., published Sept. 11, 1987. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Agents that cause proarrhythmia (proarrhythmic agents) include but are not limited to disopyramide, procainamide, n-acetyl-procainamide, quinidine, beperdil, mexiletine, propafenone, flecainide, amiodarone, bretylium, sotalol, ibutilide, dofetilide, azimilide, aprindine, ajmaline, almokalant, mibefradil, clofilium, semantilide, erythromycin, clarithromycin, Azithromycin, ampicillin, levofloxacin, moxifloxacin, sparfloxacin, gatifloxacin, grepafloxacin, trimethoprim-sulfamethoxazole, troleandomycin, pentamidine, quinine, foscarnet, fluconazole, itraconazole, ketoconazole, chloroquine, halofantrine, mefloquine, amantadine, spiramycin, astemizole, diphenhydramine, terfenadine, ebastine, hydroxyzine, doxepin, fluoxetine, desipramine, imipramine, clomipramine, paroxetine, sertralilne, venlafaxine, citalopram, ketanserin, chlorpromazine, prochlorperazine, trifluoperazine, fluphenazine, felbamate, haloperidol, droperidol, mesoridazine, pimozide, quetiapine, risperidone, thioridazine, ziprasidone, lithium, chloral hydrate, pericycline, sertindole, sultopride, zimeldine, maprotiline, felbamate, fosphenytoin, sevoflurane, bepridil, lipoflazine, prenylamine, intracoronary papaverine, isradipine, nicardipine, moexipril/hydrochlorthiazide, arsenic trioxide, tamoxifen, probucol, sumatriptan, zolmitriptan, naratriptan, indapamide thiazide, furosemide, cisapride, metoclopramide, domperidone, erythromycin, arsenic trioxide, tizanidine, tacrolimus, salmeterol, levomethadyl, pinacidil, cromakalin, aconitine, veratridine, batrachotoxin, anthopleurin A, ketanserin, vincamine, terodiline, budipine, cesium chloride, tiapride, levomethadyl acetate, cocaine, organophosphorus compounds.

The amount of antiarrhythmic agent contained in the oral dosage forms of the present invention will depend on the particular antiarrhythmic agent selected and the dosing schedule upon which the antiarrhythmic is dosed to the patient. One embodiment of the invention comprises a method for treating atrial fibrillation in a mammal in need thereof comprising orally administering to said mammal a solid oral dosage form comprising a unit dose of a pharmaceutical composition comprising a antiarrhythmic or a pharmaceutically acceptable acid, salt, ester, solvate, or polymorph thereof and from about 80 mg to about 200 mg of an aspirin or from about 1 mg to about 200 mg of a statin. In one embodiment of the invention a patient is administered from about 75 mg to about 300 mg of azimilide in combination with both an aspirin and a statin.

The instant formulations may be separate dosage formulations of the pro-arrhythmic agent and aspirin and/or stain administered concurrently (at the same time) or at different staggered times (sequentially) or the combination comprising an antiarrhythmic in combination with an aspirin and/or statin may be in a single pharmaceutical dosage formulation. The instant invention is understood to include all these options.

The daily dosage amount of the pro-arrhythmic agent are intended to be the same or similar to those amounts which are employed for the treatment of the particular disorder and that are described in either the labels of the FDA approved drugs (for example amiodorone, dofetilide, sotolol droperidol, levomethadyl, spafloxacin, thioridazine, cisapride) or in published papers on the drugs. In certain embodiments the daily dosage of dofetilide is about 125 mg to 500 mg and the daily dosage of amiodorone is from about 400 to about 1600 mg. In one embodiment the daily dosage of azimilide is about 50 mg to about 150 mg.

The daily dosage amount of the aspirin or statins are intended to be the same or similar to those amounts which are employed for inflammation or anti-hypercholesterolemic treatment, respectively, and which are described in the Physicians' Desk Reference. In one embodiment the oral dosage amount of a statin is from about 1 to 200 mg/day, preferably from about 5 to 160 mg/day. However, amounts vary depending on the potency of the statin as well as other factors. The Statin may be administered from 1 to 4 times per day, preferably once per day. As examples, simvastatin may be selected from 5 mg, 10 mg, 20 mg, 40 mg, 80 mg and 160 mg; lovastatin, 10 mg, 20 mg, 40 mg, and 80 mg; fluvastatin, 20 mg, 40 mg, and 80 mg; pravastatin, 10 mg, 20 mg, and 40 mg; and atorvastatin, 10 mg, 20 mg, and 40 mg.

The pharmaceutical compositions of the present invention may further comprise one or more pharmaceutically-acceptable excipients. The term "pharmaceutically-acceptable excipients," as used herein, means any physiologically inert, pharmacologically inactive material known to one skilled in the art, which is compatible with the physical and chemical characteristics of the active ingredient, including but not limited to the antiarrhythmic, aspirin or statin. Pharmaceutically-acceptable excipients include, but are not limited to, polymers, resins, plasticizers, fillers, lubricants, diluents, binders, disintegrants, solvents, co-solvents, surfactants, preservatives, sweetening agents, flavoring agents, pharmaceutical grade dyes or pigments, and viscosity agents.

The present invention also encompasses the use of an agent that causes pro-arrhythmia for the preparation of a medicament for the combined use with an aspirin or statin for the treatment or prevention of a disorder, such as cardiac arrhythmia, with reduced incidence of TdP; and the use of an aspirin and/or statin for the preparation of a medicament for the combined use with an agent for the treatment or prevention of a disorder, such as cardiac arrhythmia, with reduced incidence of TdP. The medicament or pharmaceutical combination comprised of the agent that may cause pro-arrhythmia and aspirin and/or statin may also be prepared with one or more additional active agents or excipients. The formulations, method and medicaments of the present invention may be used with other treatment regimens. In one embodiment, a medicament comprising azimilide and aspirin and/or statin may be administered to a person with an ICD.

Flavoring agents and dyes and pigments among those useful herein include those described in Handbook of Pharmaceutical Excipients (4th ed., Pharmaceutical Press 2003).

Suitable co-solvents include, but are not limited to, ethanol, isopropanol, and acetone.

Suitable surfactants include, but are not limited to, polyoxyethylene sorbitan fatty acid esters, polyoxyethylene monoalkyl ethers, sucrose monoesters, sodium lauryl sulfate, Tween 80®, and lanolin esters and ethers.

Suitable preservatives include, but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, and propyl paraben.

Suitable fillers include, but are not limited to, starch, lactose, sucrose, maltodextrin, and microcrystalline cellulose.

Suitable plasticizers include, but are not limited to, triethyl citrate, polyethylene glycol, propylene glycol, dibutyl phthalate, castor oil, acetylated monoglycerides, and triacetin.

Suitable polymers include, but are not limited to, hydroxypropylmethylcellulose, hydroxypropylcellulose, polyvinylpyrrolidone, and ethylcellulose.

Suitable lubricants include, but are not limited to, magnesium stearate, stearic acid, and talc.

Kits

The kits of the present invention are particularly useful for administering one or more unit doses of a solid oral dosage form comprising a pharmaceutical composition of the invention comprising an antiarrhythmic agent and an aspirin and/or statin and an appropriate continuous dosing schedule. Such kits comprise one or more unit doses of an antiarrhythmic agent and an aspirin and/or statin and a means for facilitating compliance with methods of this invention. In one embodiment, a kit of the present invention is useful for administering a unit dose of a pharmaceutical composition of the present invention according to a continuous dosing schedule. The term "continuous," as used herein, means at regular specified intervals. For example, a continuous frequency of once a month means that the active is given one day each month for an unspecified period of time or for as long as treatment is necessary.

The kits of the invention provide a convenient and effective means for assuring that the subject to be treated takes the appropriate active in the correct dosage in the correct manner. The compliance means of such kits includes any means that facilitates administering the actives according to a method of this invention. Such compliance means includes instructions, packaging, and dispensing means, and combinations thereof. The kits can also comprise a means for aiding the memory, including but not limited to a listing of the days of the week, numbering, illustrations, arrows, Braille, calendar stickers, reminder cards, or other means specifically selected by the patient.

The following are non-limiting examples of embodiments of the present invention.

Example 1

Azimilide Dihydrochloride Film-Coated Tablets, 75 mg and 125 mg are as follows:

| Ingredient | Unit Quantity (mg/tablet) | Unit Quantity (mg/tablet) |
|---|---|---|
| Core Tablet | 75 mg | 125 mg |
| Azimilide dihydrochloride | 75.0 | 125.0 |
| Lactose monohydrate NF | 359.2 | 319.1 |
| Microcrystalline cellulose NF | 133.7 | 118.7 |
| Crospovidone NF | 18.0 | 18.0 |
| Talc NF | 7.5 | 12.0 |
| Magnesium stearate NF | 6.6 | 6.6 |
| Colloidal silicon dioxide NF | 0.0 | 0.6 |
| Subtotal | 600 mg | 600 mg |
| Film Coating | | |
| Dri-Klear | 14.18 | 14.200 |
| Chroma-Tone White (DDB-7536W) | 3.82 | 3.650 |
| Ferric oxide red, NF | | 0.175 |
| Subtotal | 18 mg | 18 mg |

Target Total Tablet Weight = 618 mg

Example 2

Clinical trials are conducted where 5375 patients receive oral doses of azimilide. Patients are administered azimilide using a 3-day, twice daily loading regimen of 150-250 mg/day followed by a daily maintenance regimen (75-125 mg/day) of ½ of the loading dose, or are given daily azimilide (75, 100 or 125 mg/day) without a loading regimen. Overall about 75% of the patients are men and about 25% are women. Two cases of TdP are found in placebo-assigned patients and 54 azimilide-associated cases of TdP. Lack of aspirin use or lack of statin use is more frequent in azimilide patients with TdP. A total of 1191 (22%) patients (243 [16%] females and 948 [25%] males) are taking statins and aspirin as concomitant medication. Among the 54 patients (30 females and 24 males) who experienced TdP, 35% are on aspirin, 20% are on statins and only 11% are taking both a statin and aspirin as concomitant medication.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for reducing the incidence of azimilide-induced torsades de pointes consisting essentially of administering azimilide and aspirin to a patient having cardiac arrhythmia.

2. The method of claim 1, wherein the azimilide is administered daily in amounts from about 75 mg to about 300 mg.

3. The method of claim 1, wherein the aspirin is administered daily in amounts from about 80 mg to about 200 mg.

4. The method of claim 2, wherein the azimilide is administered daily in an amount of about 75 mg.

5. The method of claim 2, wherein the azimilide is administered daily in an amount of about 100 mg.

6. The method of claim 2, wherein the azimilide is administered daily in an amount of about 125 mg.

7. A method for reducing the incidence of azimilide-induced torsades de pointes consisting essentially of administering azimilide and a statin to a patient having cardiac arrhythmia.

8. The method of claim 7, wherein the azimilide is administered daily in amounts from about 75 mg to about 300 mg.

9. The method of claim 8, wherein the azimilide is administered daily in an amount of about 75 mg.

10. The method of claim 8, wherein the azimilide is administered daily in an amount of about 100 mg.

11. The method of claim 8, wherein the azimilide is administered daily in an amount of about 125 mg.

12. A method for reducing the incidence of azimilide-induced torsades de pointes consisting essentially of administering azimilide, aspirin, and a statin to a patient having cardiac arrhythmia.

13. The method of claim 12, wherein the azimilide is administered daily in amounts from about 75 mg to about 300 mg.

14. The method of claim 13, wherein the azimilide is administered daily in an amount of about 75 mg.

15. The method of claim 13, wherein the azimilide is administered daily in an amount of about 100 mg.

16. The method of claim 13, wherein the azimilide is administered daily in an amount of about 125 mg.

17. The method of claim 12, wherein the aspirin is administered daily in amounts from about 80 mg to about 200 mg.

18. The method of claim 1, wherein the cardiac arrhythmia is atrial fibrillation.

19. The method of claim 7, wherein the cardiac arrhythmia is atrial fibrillation.

20. The method of claim 12, wherein the cardiac arrhythmia is atrial fibrillation.

21. The method of claim 1, wherein the cardiac arrhythmia is ventricular arrhythmia.

22. The method of claim 7, wherein the cardiac arrhythmia is ventricular arrhythmia.

23. The method of claim 12, wherein the cardiac arrhythmia is ventricular arrhythmia.

* * * * *